(12) United States Patent
Hutchings et al.

(10) Patent No.: US 11,826,146 B2
(45) Date of Patent: Nov. 28, 2023

(54) PSYCHOMOTOR VIGILANCE TESTING FOR PERSONS TASKED WITH MONITORING AUTONOMOUS VEHICLES

(71) Applicant: WAYMO LLC, Mountain View, CA (US)

(72) Inventors: Keith Hutchings, San Jose, CA (US); Julien Mercay, Redwood City, CA (US); Nirmal Patel, Sunnyvale, CA (US); Ilmo van der Lowe, Fremont, CA (US); Vasily Starostenko, Fremont, CA (US); Samrat Kansara, San Francisco, CA (US)

(73) Assignee: Waymo LLC, Mountain View, CA (US)

( * ) Notice: Subject to any disclaimer, the term of this patent is extended or adjusted under 35 U.S.C. 154(b) by 1084 days.

(21) Appl. No.: 16/598,752

(22) Filed: Oct. 10, 2019

(65) Prior Publication Data

US 2021/0106266 A1    Apr. 15, 2021

(51) Int. Cl.
*A61B 5/00*     (2006.01)
*A61B 5/16*     (2006.01)
(Continued)

(52) U.S. Cl.
CPC ............ *A61B 5/18* (2013.01); *A61B 5/162* (2013.01); *A61B 5/165* (2013.01); *A61B 5/7267* (2013.01); *A61B 5/7282* (2013.01); *B60K 28/06* (2013.01)

(58) Field of Classification Search
CPC ........... A61B 5/18; A61B 5/162; A61B 5/165; A61B 5/7267; A61B 5/7282;
(Continued)

(56) References Cited

U.S. PATENT DOCUMENTS 6,575,902 B1 *   6/2003   Burton .................. B60W 40/08
                                              600/595
10,363,945 B2    7/2019   Huang et al.
(Continued)

FOREIGN PATENT DOCUMENTS

KR    20190095199 A    8/2019
WO     2019122967 A1   6/2019

OTHER PUBLICATIONS

International Search Report and Written Opinion for Application No. PCT/US2020/054771 dated Jan. 20, 2021.
(Continued)

*Primary Examiner* — Carl H Layno
*Assistant Examiner* — Anh-Khoa N Dinh
(74) *Attorney, Agent, or Firm* — Botos Churchill IP Law

(57) ABSTRACT

Assessing a likelihood of a person experiencing a fatigue event when the person tasked with monitoring a vehicle operating in an autonomous driving mode may include receiving a set of response times for a psychomotor vigilance test administered to the person. The test may include a plurality of trials which involve a person lifting a finger from a user input device. Whether the person passed or failed each trial of the set of trials may be determined. A model trained using data from prior psychomotor vigilance tests administered to the person may be identified for the person. Results of the determinations of whether the person passed or failed each trial of the set of trials may be input into the model in order to determine a value representative of a likelihood of a fatigue event. An intervention response may be initiated based on the value.

22 Claims, 9 Drawing Sheets

(51) Int. Cl.
*A61B 5/18* (2006.01)
*B60K 28/06* (2006.01)

(58) Field of Classification Search
CPC ... A61B 5/1118; A61B 5/7475; A61B 5/7275;
A61B 5/7225; A61B 5/6898; A61B
5/6801; A61B 5/4875; A61B 5/4866;
A61B 5/4857; B60K 28/06; G16H 40/63;
G16H 50/30; G16H 20/30; G16H 30/20;
G16H 40/67; G16H 50/20; G16H 10/60;
G16H 40/20; G16H 50/50; G16H 50/70;
A61F 2/86; A61F 2002/8483; A61F
2250/0002; A61F 5/02; G06K 19/07762;
G06K 19/06037; G06K 19/06065; G06K
19/0614; G06K 2019/0629; G06K
19/025; G06F 2111/10; G06F 30/20;
H04W 4/12; H04M 1/72412; H03K
21/023; H03K 21/026; H03K 23/542;
H03K 3/00; H03K 4/00; H03K 5/00;
H03K 6/00; H03K 7/00; H03K 9/00;
H03K 11/00; H03K 12/00; H03K 17/00;
H03K 19/00; H03K 21/00; H03K 23/00;
H03K 25/00; H03K 27/00
See application file for complete search history.

(56) References Cited

U.S. PATENT DOCUMENTS

| | | | |
|---|---|---|---|
| 10,379,535 | B2 | 8/2019 | Migneco et al. |
| 2015/0375757 | A1 | 12/2015 | Schiek et al. |
| 2016/0148523 | A1 | 5/2016 | Winston |
| 2017/0188979 | A1 | 7/2017 | Volpe |
| 2017/0355377 | A1 | 12/2017 | Vijaya Kumar et al. |
| 2018/0072327 | A1 | 3/2018 | Seppelt et al. |
| 2018/0178808 | A1 | 6/2018 | Zhao et al. |
| 2019/0152492 | A1 | 5/2019 | El Kaliouby et al. |
| 2019/0300034 | A1* | 10/2019 | Molne ............ B61L 25/021 |

OTHER PUBLICATIONS

Nachiket Deo and Mohan M. Trivedi, Looking at the Driver/Rider in Autonomous Vehicles to Predict Take-Over Readiness, arXiv:1811. 06047v1 [cs.CV] Nov. 14, 2018.

* cited by examiner

PSYCHOMOTOR VIGILANCE TESTING FOR PERSONS TASKED WITH MONITORING AUTONOMOUS VEHICLES

BACKGROUND

Autonomous vehicles, such as vehicles which do not require a human driver when operating in an autonomous driving mode, may be used to aid in the transport of passengers or items from one location to another. Testing of these vehicles typically involves a "test driver" who is tasked with monitoring the autonomous vehicle to ensure that the vehicle is operating safely. For instance, a person may be expected to monitor the vehicle and the vehicle's environment while the vehicle operates in the autonomous driving mode and to take control of the vehicle if there is an emergency or other such situation. Supervision of such vehicles is known to increase a person's susceptibility to fatigue, when it's due to sleep deprivation, poor quality sleep, fatigue induced by the monitoring itself, or the interaction of these contributing sources of fatigue.

Psychomotor vigilance tests (PVTs) may be used to test a person's current state of awareness by way of patterns in his or her reaction times. For instance, a PVT may require a person to perform a specific action, such as pressing a button, as soon as the person recognizes that a particular image or message is displayed or a particular audio is played. Current PVTs have demonstrated that a single set of PVT evaluation criteria can be used to predict the future task performance of a group of fatigued people (such as driving performance). However, individuals may vary greatly in their baseline PVT performance, which may make existing PVTs less sensitive to some persons' fatigued responses and overly sensitive to other persons' fatigued responses. This, in turn, may result in group-level PVT pass/fail criteria to produce false negatives for some and false positives for others, respectively.

SUMMARY

One aspect of the disclosure provides a method of assessing a likelihood of a person experiencing a fatigue event, the person tasked with monitoring a vehicle operating in an autonomous driving mode. The method includes receiving, by one or more server computing devices, a set of response times for a psychomotor vigilance test administered to the person, the test including a set of trials; determining, by the one or more server computing devices, whether the person passed or failed each trial of the set of trials; identifying, by the one or more server computing devices, a model associated with the person, the model being trained using data from prior psychomotor vigilance tests administered to the person; inputting, by the one or more server computing devices, results of the determinations of whether the person passed or failed each trial of the set of trials into the model in order to determine a value representative of a likelihood of a fatigue event; and initiating, by the one or more server computing devices, an intervention response based on the value.

In one example, the method also includes determining the intervention response by comparing the value to one or more threshold values. In another example, the method also includes determining a score for the test based on the determinations of whether the person passed or failed each trial of the set of trials, and the results include the score. In this example, the score represents a passing or failing rate for the person. In another example, the method also includes inputting date and time information for the set of trials into the model in order to determine the value. In another example, the method also includes inputting shift information about a relative point in time for a shift for monitoring the vehicle of the person for the test into the model in order to determine the value. In another example, the method also includes inputting an amount of time since a last break of the person for the test into the model in order to determine the value. In another example, the method also includes inputting information identifying where a person is with respect to his or her circadian rhythm, for the test into the model in order to determine the value. In another example, the method also includes determining a threshold amount of time based on whether the person is left-handed or right-handed, and determining whether the person passed or failed each trial of the set of trials is based on the threshold amount of time. In another example, the method also includes determining a threshold amount of time using a model of how response times change over time due to muscle fatigue, and determining whether the person passed or failed each trial of the set of trials is based on the threshold amount of time. In another example, the method also includes determining a threshold amount of time using a model of how response times change over time for the person, and determining whether the person passed or failed each trial of the set of trials is based on the threshold amount of time. In another example, the method also includes determining a threshold amount of time using a model of how response times change over time for a similarly situated person, and determining whether the person passed or failed each trial of the set of trials is based on the threshold amount of time. In another example, the method also includes determining a threshold amount of time is based on an orientation of a user input device used to administer the set of trials, and determining whether the person passed or failed each trial of the set of trials is based on the threshold amount of time. In another example, the method also includes determining a threshold amount of time is based on an orientation of a user input device used to administer the set of trial, and determining whether the person passed or failed each trial of the set of trials is based on the threshold amount of time. In another example, the method also includes, once an intervention response is identified, sending one or more signals to one or more of the computing devices of the vehicle, a PVT system that administered the test, and a computing device of a remote assistance operator in order to initiate the identified intervention response. In this example, the signal includes instructions for the testing system to administer a second test. In addition, the signal includes instructions for the vehicle to stop operating in the autonomous driving mode. In addition, the signal includes instructions for the vehicle to prevent the person from operating the vehicle in a manual driving mode. In addition or alternatively, the signal enables the person to communicate with the remote assistance operator.

Another aspect of the disclosure provides a method of training a model for estimating a likelihood of a fatigue event for a person tasked with monitoring a vehicle operating in an autonomous driving mode. The method includes accessing, by one or more server computing devices, results from a plurality of sets of psychomotor vigilance test administered to the person at different points in time, the results including response times for the person; determining, by the one or more server computing devices, scores for each of the sets of tests based on the results; accessing, by the one or more server computing devices, information from a remote monitoring system identifying estimations of the person's amount of fatigue at different times; determining, by the one or more server computing devices, whether the information indicates that the person experienced one or more fatigue events; and using, by the one or more server computing devices, the determined scores and the determination of whether the information indicates that the person experienced one or more fatigue events to train a model individualized to the person such that when data from a set of tests are input into the model, the model outputs a value indicative of a likelihood of the person experiencing a fatigue event.

Another aspect of the disclosure provides a method of administering a psychomotor vigilance test to a person tasked with monitoring a vehicle operating in an autonomous driving mode. The method includes providing, by one or more processors, for display to the person, a visual stimulus on a touch-sensitive display while the person is resting a finger on the display; determining, by one or more processors, based on feedback from the touch-sensitive display, a point in time when the finger was removed from the display; measuring, by one or more processors, an amount of time for the person to remove the finger from the display between when the visual stimulus was provided and the point in time; and sending, by the one or more processors, the amount of time to a remote computing system in order to determine a likelihood of a fatigue event while the person is tasked with monitoring the vehicle.

In one example, each stimulus and amount of time correspond to a single trial, and wherein the test includes a plurality of trials. In another example, the method also includes providing instructions, by the one or more processors via the display, to the person to place the finger on the display prior to providing the visual stimulus.

DETAILED DESCRIPTION

Overview

Figure 1:
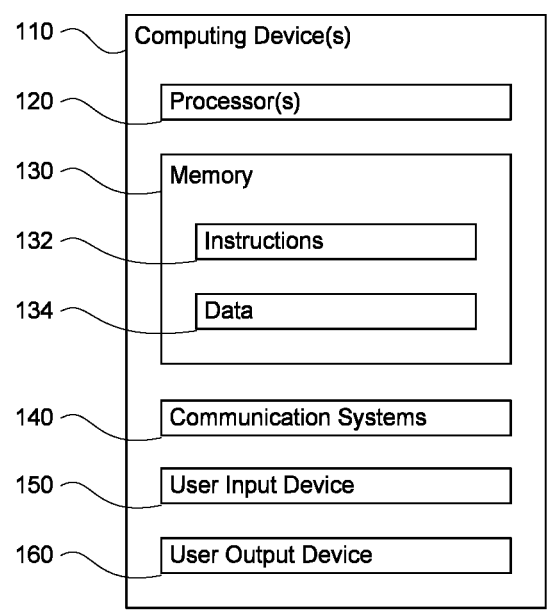
FIG. 1 is an example of a PVT system.

The technology relates to psychomotor vigilance test (PVTs) for persons who are tasked with monitoring the driving of a vehicle operating in an autonomous driving mode. For instance, a person may be expected to monitor the vehicle and the vehicle's environment while the vehicle operates in the autonomous driving mode and to take control of the vehicle if there is an emergency or other such situation. Supervision of such vehicles is known to increase a person's susceptibility to fatigue, when it's due to sleep deprivation, poor quality sleep, fatigue induced by the monitoring itself, or the interaction of these contributing sources of fatigue. To test a person's current state of awareness by way of patterns in his or her reaction times, a PVT may require a person to perform a specific action, such as press or lifting a finger away from a button or a screen as soon as the person recognizes that a particular image or message is displayed or a particular audio is played. Current PVTs have demonstrated that a single set of PVT evaluation criteria can be used to predict future task performance (such as driving performance). However, individuals may vary greatly in their baseline PVT performance, which may make existing PVTs less sensitive to some persons' responses and overly sensitive to other persons' responses. This, in turn, may result in group-level PVT pass/fail criteria that produce false negatives for some and false positives for others, respectively.

A testing system may include an output device, such as a touchscreen and/or speaker, as well as a user input device. The user input device may be connected to a computing device that can measure a time between when information is displayed on the output device and when a person completes a trial of a test, for instance by tapping with a finger on the touchscreen or alternatively by lifting the finger from the touchscreen. For instance, the computing device may provide a stimulus, such as displaying information on a screen, and start a timer or counter. When the person's finger is removed from the touchscreen, the counter may be used to determine how long it takes for the user input device to register a response of the person for the trial. This may correspond to a response time, which in effect accounts for both a reaction time (when the person recognizes the stimulus) and the physical movement time (the time required for a person to move his or her finger). The response time may then be compared to some pass/fail criteria such as a threshold amount of time to determine whether the person has passed or failed the trial.

As noted above, the testing system may be employed within a vehicle having an autonomous driving mode. As such, the testing system may be able to communicate with the computing devices of the vehicle as well as various remote computing devices either directly or indirectly via the computing devices of the vehicle.

To address the aforementioned short-comings related to false positives (or rather failures that should not actually be considered failures), the features described here may reduce error due to counting movement time as response time and create individualized pass/fail criteria that account for error due to differing baseline performance between individuals. For instance, rather than simply monitoring a press of a button or screen, each trial of a test may be configured as a finger lift. In this regard, each trial of a test may begin with a person's finger rested on a touchscreen or other touch sensitive device.

A person may take a plurality of tests at different times of day during different shifts. The reaction times may be sent by the testing system to a remote server computing device. In some instances, a plurality of trials from a single test may be scored. The scoring may be based on the response times.

This information may be combined with other signals. For instance, an in-vehicle or remote monitoring system may be used to determine a person's fatigue. As another instance, the testing system may include an option for a person to self-report the state of his or her fatigue on the same or a different assessment scale.

Results from a particular person's PVTs as well as the other signals may be used to train a model. The model may be a regression model or a statistical model trained by one or more server computing devices. The PVT data may include both the dates, times, and point in time relative to the person's shift that a series of PVTs was performed as well as the response times and/or scores. This PVT data may be used as training inputs. The data from the in-car or remote monitoring system and/or the self-reported data may be used to determine whether a set of PVTs corresponds to a fatigue event (e.g. stop paying attention or even falling asleep). These determinations (fatigue event or no fatigue event) may be used as the training outputs.

The model may be trained such that inputting new PVT data and point with respect to his or her shift will provide an estimate of a person's current and/or future state of fatigue. The more PVT data and other signals used to train the model the more accurate the probability estimation that the person will have a fatigue event. The model may then be associated with the person, for instance using an identifying code or other information, and saved for later retrieval.

When and how often the testing system administers a test may vary depending upon the situation. To administer a test, the vehicle's computing devices may send a signal to the testing system when such situations occur. The testing system may test a person by administering a set of trials and evaluating the person's response times for those trials as described above. The response times as well as date and time information for the trials of a test, shift information about the relative point in the person's shifts, as well as any of the additional information discussed above (if available) may then be sent to and received by the remote server computing device.

The remote server computing device may then use the reaction times to determine whether the person passed or failed each of the set of trials of a test. This may also include determining a score for the trials of the set. The model associated with the particular person, which as noted above, was trained using data from prior tests administered to that person as well as other signals as discussed above may be identified. The results of the determinations of whether the person passed or failed each PVT of the set of PVTs or alternatively, the response times, may be input into the model in order to determine a value representative of a likelihood of a fatigue event.

In order to determine and initiate an intervention response, the value may then be compared to a threshold value or plurality of threshold values to determine whether and what type of intervention response to take. Once an intervention response is identified, the server computing devices may send a signal to the computing devices of the vehicle, the PVT system, and/or a remote assistance operator in order to initiate the identified intervention response. Various different types of intervention responses may be employed.

The features described herein may provide for a reliable and effective system for identifying possible fatigue events in persons tasked with monitoring the driving of a vehicle operating in an autonomous driving mode. For instance, because the model is trained specific to a particular person or a similarly situated person, the model may be more likely to identify outlier situations. Moreover, because the threshold amount of time used to determine whether a person has passed or failed a particular PVT can be adjusted to accommodate for the particular person or similarly situated persons, this may further increase the effectiveness of the system reduce false positives. In other words, threshold amounts of time may be set in a way that accounts for individual variance, for instance, due to muscle fatigue.

Example Systems

A testing system may include one or more computing devices 110 having one or more processors 120 and memory 130 storing instructions 132 and data 134. The memory 130 stores information accessible by the one or more processors 120, including instructions 132 and data 134 that may be executed or otherwise used by the processor 120. The memory 130 may be of any type capable of storing information accessible by the processor, including a computing device-readable medium, or other medium that stores data that may be read with the aid of an electronic device, such as a hard-drive, memory card, ROM, RAM, DVD or other optical disks, as well as other write-capable and read-only memories. Systems and methods may include different combinations of the foregoing, whereby different portions of the instructions and data are stored on different types of media.

The instructions 132 may be any set of instructions to be executed directly (such as machine code) or indirectly (such as scripts) by the processor. For example, the instructions may be stored as computing device code on the computing device-readable medium. In that regard, the terms "instructions" and "programs" may be used interchangeably herein. The instructions may be stored in object code format for direct processing by the processor, or in any other computing device language including scripts or collections of independent source code modules that are interpreted on demand or compiled in advance. Functions, methods and routines of the instructions are explained in more detail below.

The data 134 may be retrieved, stored or modified by processor 120 in accordance with the instructions 132. For instance, although the claimed subject matter is not limited by any particular data structure, the data may be stored in computing device registers, in a relational database as a table having a plurality of different fields and records, XML documents or flat files. The data may also be formatted in any computing device-readable format.

The one or more processors 120 may be any conventional processors, such as commercially available CPUs or GPUs. Alternatively, the one or more processors may be a dedicated device such as an ASIC or other hardware-based processor. Although FIG. 1 functionally illustrates the processor, memory, and other elements of computing device 110 as being within the same block, it will be understood by those of ordinary skill in the art that the processor, computing device, or memory may actually include multiple processors, computing devices, or memories that may or may not be stored within the same physical housing. For example, memory may be a hard drive or other storage media located in a housing different from that of computing device 110. Accordingly, references to a processor or computing device will be understood to include references to a collection of processors or computing devices or memories that may or may not operate in parallel.

The computing device 110 may also include an output device 160, such as a touchscreen and/or speaker, as well as a user input device 150, such as a touchscreen, button or other touch sensitive device. In this regard, the output device and the user input device may be the same device (e.g. a touchscreen). The user input device 150 may be incorporated into or connected to a computing device, such as computing device 110, that can measure a time between when information is displayed on the output device and when a person completes a trial of a test, for instance by tapping with a finger on the touchscreen or alternatively by lifting the finger from the touchscreen. For instance, the computing device 110 may provide a stimulus, such as displaying information on a screen, and start a timer or counter. When the person's finger is removed from the touchscreen, the counter may be used to determine how long it takes for the user input device 150 to register a response of the person for the trial. This may correspond to a response time, which in effect accounts for both a reaction time (when the person recognizes the stimulus) and the physical response time (when the person moves his or her finger). The response time may then be compared to some pass/fail criteria such as a threshold amount of time to determine whether the person has passed or failed the trial.

As an example, in a single test, there may be as many as 60-70 trials which all together may take approximately 3 minutes to complete. For instance, the tests may utilize an inter-stimulus-interval (ISA) of 1-4 seconds, varying randomly between trials/stimuli. If the ISA were to be set to 1-3 seconds, there would be many more trials within the same test (currently at 3 minutes). Additionally, the test length can be increased or decreased, which would also increase or decrease the total number of trials for the test.

The testing system 100 may also include a communications system 140 that enables the testing system 100 to communicate with other computing devices. For example, the communication system may include wired and/or wireless connections (such as transmitters and receivers), that enable the testing system to communicate with other computing devices. As an example, the communications system may enable the testing system to use various protocols including short range communication protocols such as Bluetooth, Bluetooth LE, the Internet, World Wide Web, intranets, virtual private networks, wide area networks, local networks, private networks using communication protocols proprietary to one or more companies, Ethernet, WiFi and HTTP, and various combinations of the foregoing. Such communication may be facilitated by any device capable of transmitting data to and from other computing devices, such as modems and wireless interfaces.

Figure 2:
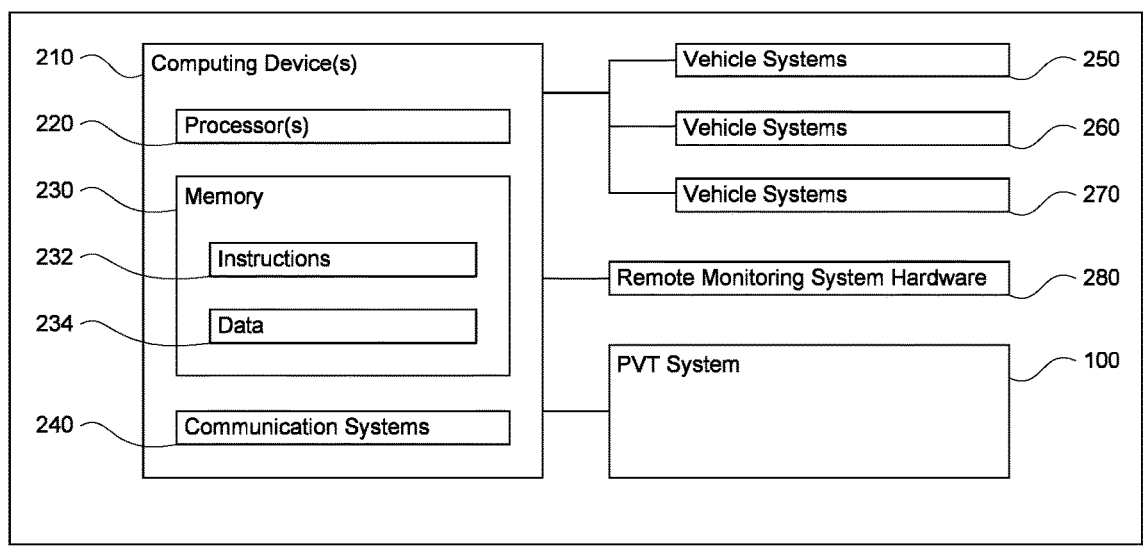
FIG. 2 is a functional diagram of an example vehicle in accordance with an exemplary embodiment.
Figure 3:
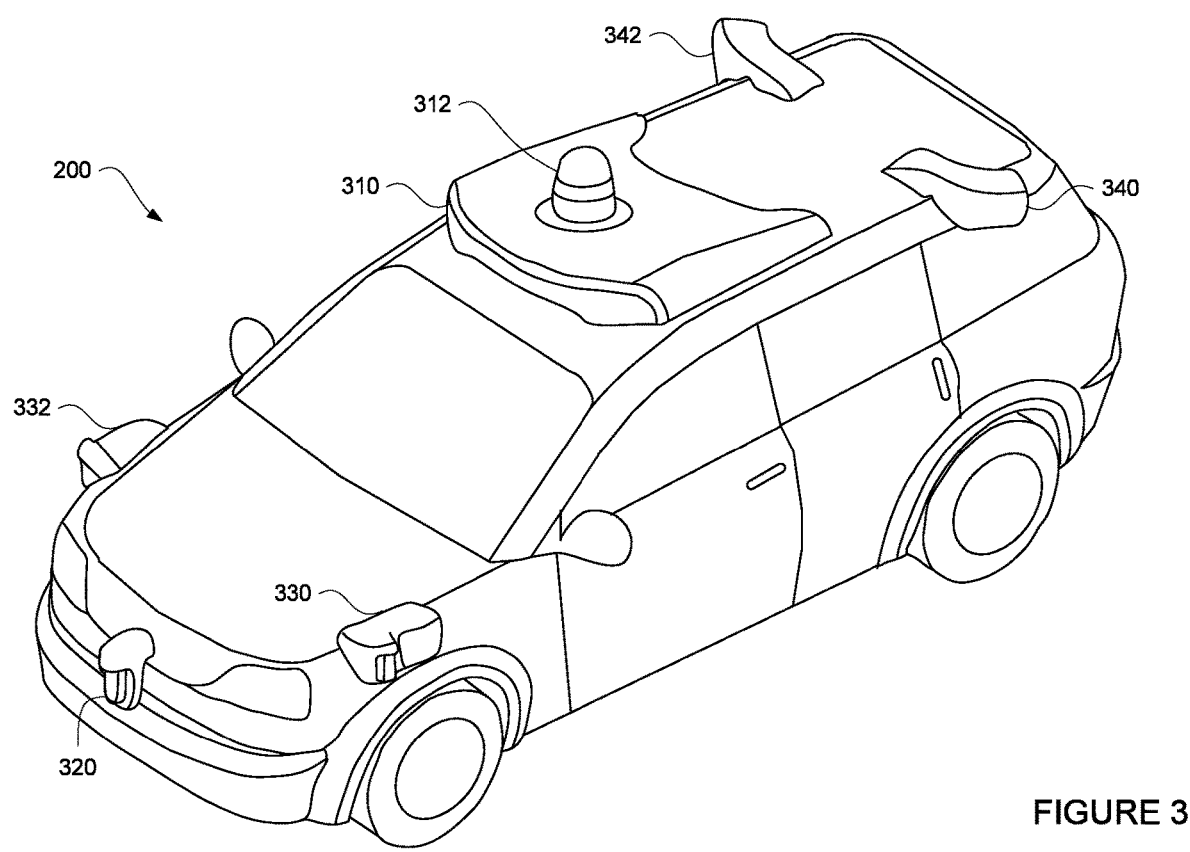
FIG. 3 is an example external view of a vehicle in accordance with aspects of the disclosure.

As noted above, the testing system may be employed within a vehicle having an autonomous driving mode. FIG. 2 is an example block diagram of a vehicle 200, and FIG. 3 is an example view of the vehicle 200. In this example, the vehicle 200 is a vehicle having an autonomous driving mode as well as one or more additional driving modes, such as a semiautonomous or manual driving mode. While certain aspects of the disclosure are particularly useful in connection with specific types of vehicles, the vehicle may be any type of vehicle including, but not limited to, cars, trucks, motorcycles, buses, recreational vehicles, etc.

Turning to FIG. 2, the computing devices 110 of the testing system may be in communication with one or more computing devices 210 of the vehicle. The one or more computing devices 210 may include one or more processors 220, memory 230 storing instructions 232 and data 234, and other components typically present in general purpose computing devices. These processors, memory, instructions and data may be configured the same or similarly to the processors 120, memory 130, instructions 132, and data 134.

In one aspect the computing devices 210 may be part of an autonomous control system capable of communicating with various components of the vehicle in order to control the vehicle in an autonomous driving mode. For example, returning to FIG. 2, the computing devices 210 may be in communication with various systems 250, 260, 270 via wired or wireless connections. As an example, these systems may correspond to a deceleration system, an acceleration system, a steering system, a routing system for determining a route for the vehicle to follow between two or more locations, and planning system for planning a trajectory, a positioning system, a perception system for detecting objects in the vehicle's environment, etc. which the computing devices can use to control the vehicle 200 in the autonomous and semiautonomous driving modes.

The vehicle 200 may also include remote monitoring system 280. This system may include hardware features such as video cameras, microphones and speakers as well as one or more computing devices and communications system which may be configured the same or similarly to computing device 110 and communications system 140. The hardware features may be used to enable a remote operator to "check-in" on a test driver as well as to enable two-way communications between the remote operator and the test driver.

Turning to FIG. 3, as an example, the vehicle 200 includes a roof-top housing 310 and dome housing 312 may include a LIDAR sensor as well as various cameras and radar units. In addition, housing 320 located at the front end of the vehicle 200 and housings 330, 332 on the driver's and passenger's sides of the vehicle may each store a LIDAR sensor. For example, housing 330 is located in front of a driver door 360. Vehicle 100 also includes housings 340, 342 for radar units and/or cameras also located on the roof of vehicle 200. Additional radar units and cameras (not shown) may be located at the front and rear ends of vehicle 200 and/or on other positions along the roof or roof-top housing 310.

The computing devices 210 may include a communications system 240 which may be the same or similar to communications system 140. The communications system may enable the computing devices 210 to communicate with other devices remote from the vehicle. In this way, information from the testing system 100 may be sent to remote devices. As such, the testing system 100 may be able to communicate with the computing devices 210 of the vehicle as well as various remote computing devices, such as those computing devices that are a part of the autonomous vehicle service as well as other computing devices, either directly or indirectly via the computing devices of the vehicle.

Figure 4:
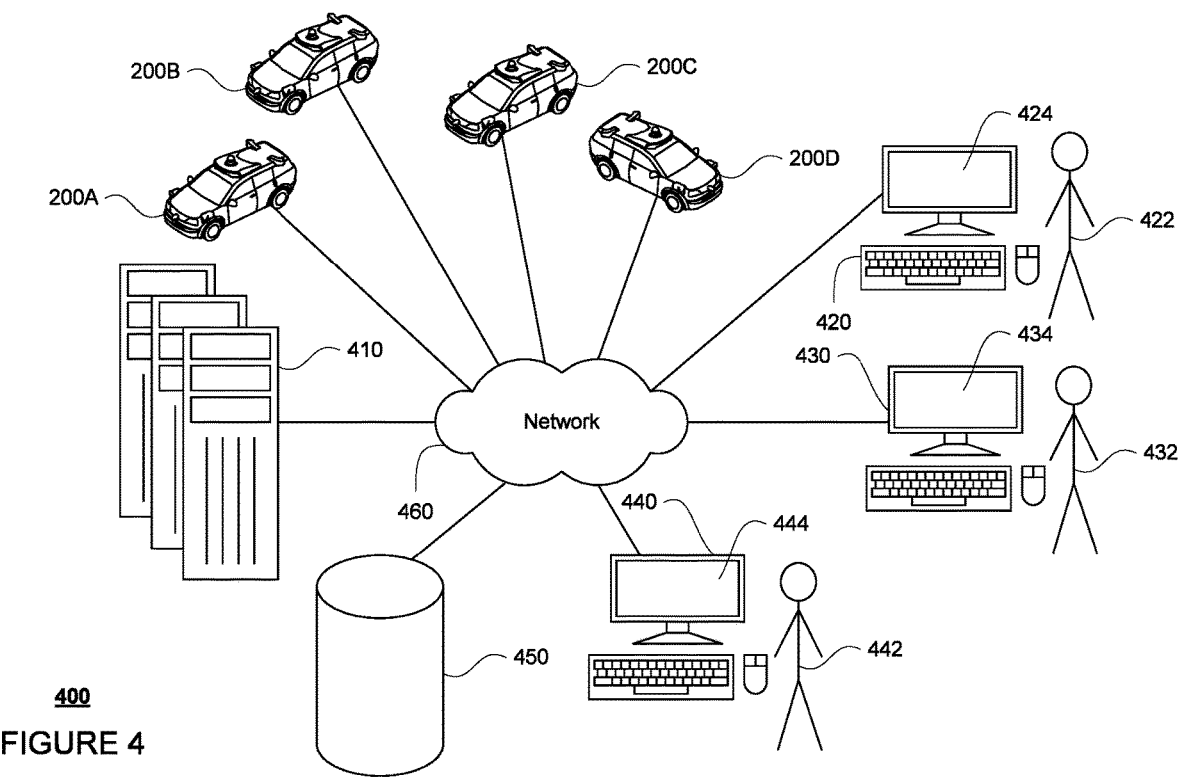
FIG. 4 is an example pictorial diagram of a system in accordance with aspects of the disclosure.
Figure 5:
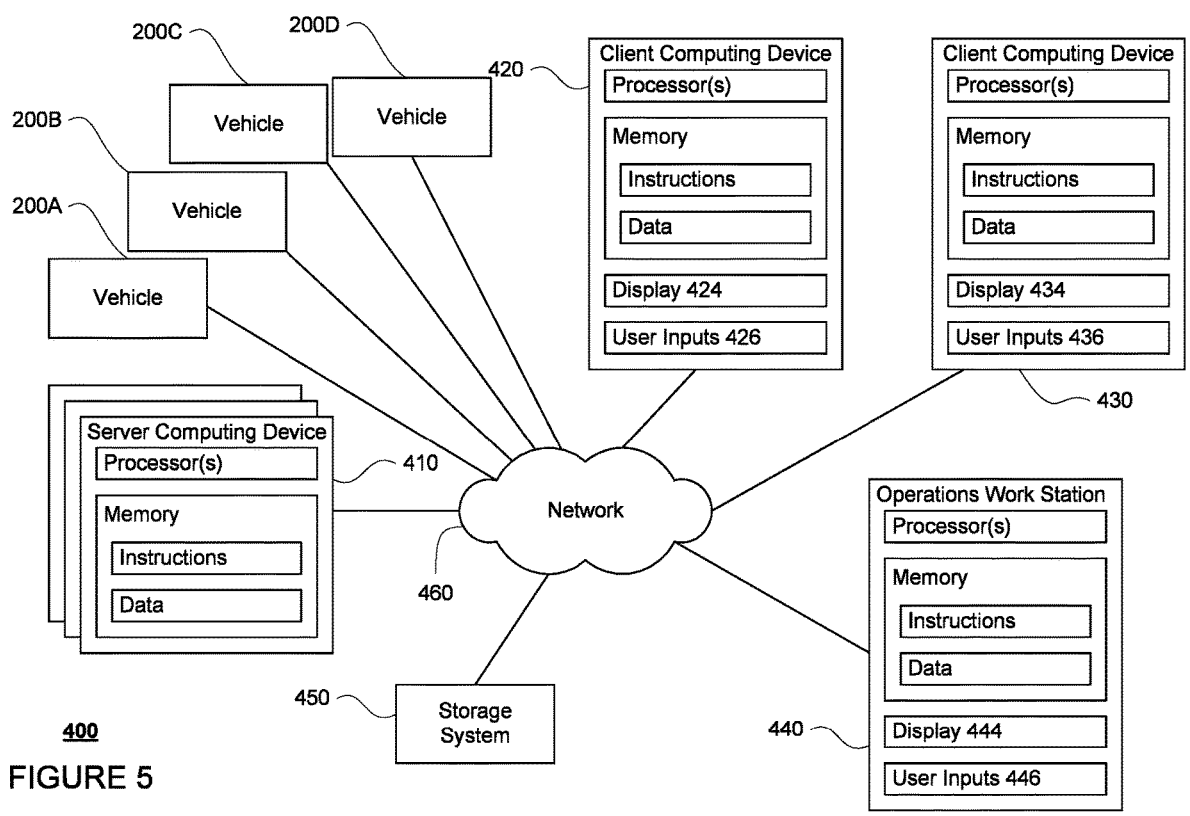
FIG. 5 is an example block diagram of the system of FIG. 4.

FIGS. 4 and 5 are pictorial and functional diagrams, respectively, of an example system 400 that includes a plurality of computing devices 410, 420, 430, 440 and a storage system 450 connected via a network 460. System 400 also includes vehicles 200A, 200B, 200C, 200D, which may be configured the same as or similarly to vehicle 200. Although only a few vehicles and computing devices are depicted for simplicity, a typical system may include significantly more.

As shown in FIG. 4, each of computing devices 410, 420, 430, 440 may include one or more processors, memory, data and instructions. Such processors, memories, data and instructions may be configured similarly to one or more processors 120, memory 130, data 134, and instructions 132 of computing device 110.

The network 460, and intervening nodes, may include various configurations and protocols including short range communication protocols such as Bluetooth, Bluetooth LE, the Internet, World Wide Web, intranets, virtual private networks, wide area networks, local networks, private networks using communication protocols proprietary to one or more companies, Ethernet, WiFi and HTTP, and various combinations of the foregoing. Again, communication may be facilitated by any device capable of transmitting data to and from other computing devices, such as modems and wireless interfaces.

In one example, one or more computing devices 410 may include one or more server computing devices having a plurality of computing devices, e.g., a load balanced server farm, that exchange information with different nodes of a network for the purpose of receiving, processing and transmitting the data to and from other computing devices. For instance, one or more computing devices 410 may include one or more server computing devices that are capable of communicating with computing device 210 of vehicle 200 or a similar computing device of other vehicles as well as computing devices 420, 430, 440 via the network 460. For example, each of the vehicles 200A, 200B, 200C, 200D, may correspond to vehicle 200 and may be a part of a fleet of vehicles of the autonomous vehicle service that can be dispatched by server computing devices 410 to various locations. In this regard, the server computing devices 410 may function (in conjunction with storage system 450) as a dispatching system for the autonomous vehicle service which can be used to dispatch vehicles such as vehicle 200 and vehicle 200A to different locations in order to pick up and drop off passengers. In addition, server computing devices 410 may use network 460 to transmit and present information to a person, such as people 422, 432, 442 on a display, such as displays 424, 434, 444 of computing devices 420, 430, 440. In this regard, computing devices 420, 430, 440 may be considered client computing devices.

As shown in FIG. 4, each client computing device 420, 430, 440 may be a personal computing device intended for use by a person 422, 432, 442, and have all of the components normally used in connection with a personal computing device including a one or more processors (e.g., a central processing unit (CPU)), memory (e.g., RAM and internal hard drives) storing data and instructions, a display such as displays 424, 434, 444 (e.g., a monitor having a screen, a touch-screen, a projector, a television, or other device that is operable to display information), and user input devices 426, 436, 446 (e.g., a mouse, keyboard, touchscreen or microphone). The client computing devices may also include a camera for recording video streams, speakers, a network interface device, and all of the components used for connecting these elements to one another.

Although the client computing devices 420, 430, and 440 may each comprise a full-sized personal computing device, they may alternatively comprise mobile computing devices capable of wirelessly exchanging data with a server over a network such as the Internet. By way of example only, the client computing devices may include a mobile phone or a device such as a wireless-enabled PDA, a tablet PC, a wearable computing device or system, or a netbook that is capable of obtaining information via the Internet or other networks.

Each of the client computing devices may be remote monitoring work station used by an administrator or remote assistance operator (e.g. people 422, 432, 444) to provide concierge or remote assistance services to test drivers of vehicles 200A, 200B, 200C, 200D. For example, a representative 442 may use the remote monitoring workstation 440 to communicate via a telephone call or audio connection with people through their respective client computing devices or vehicles 200A, 200B, 200C, 200D, in order to ensure the safe operation of vehicles 100 and 100A and the safety of the test drivers as described in further detail below. Although only a few remote monitoring workstation 440 is shown in FIGS. 4 and 5, any number of such work stations may be included in a typical system.

As with memory 130, storage system 450 can be of any type of computerized storage capable of storing information accessible by the server computing devices 410, such as a hard-drive, memory card, ROM, RAM, DVD, CD-ROM, write-capable, and read-only memories. In addition, storage system 450 may include a distributed storage system where data is stored on a plurality of different storage devices which may be physically located at the same or different geographic locations. Storage system 450 may be connected to the computing devices via the network 460 as shown in FIGS. 3 and 4, and/or may be directly connected to or incorporated into any of the computing devices 410, 420, 430, 440, etc.

The storage system 450 may be configured to store various information. This information may include the status (serving a trip, passengers, etc.), current locations, and expected future locations of the vehicles of the fleet. The information may also include data associated with a particular test driver. For instance, each test driver identified in the storage system may be associated with one or more models (or model parameter values for use with a generic model for all test drivers), reaction times, scores, dates and times of PVTs, shift information, fatigue information from remote monitoring system(s) and/or self-reported data, as well as additional information as discussed further below.

Example Methods

In addition to the operations described above and illustrated in the figures, various operations will now be described. It should be understood that the following operations do not have to be performed in the precise order described below. Rather, various steps can be handled in a different order or simultaneously, and steps may also be added or omitted.

As noted above, to address the aforementioned shortcomings related to false positives (or rather failures that should not actually be considered failures), the features described here may reduce error due to counting movement time as response time and create individualized pass/fail criteria that account for error due to differing baseline performance between individuals. For instance, rather than simply monitoring a press of a button or screen, each trial of a test may be configured as a finger lift. For example, if a person taking a test holds their finger sometimes at 1 inch and sometimes at 3 inches away, the variation in movement time will be counted as variance in reaction time even though in both cases the person may have begun to react equally as fast. In this regard, each trial of a test may begin with a person's finger placed, rested or otherwise positioned on a touchscreen or other touch sensitive device. Therefore, the initial conditions for each trial may be identical or nearly identical because movement distance is held constant over all of the tests and all of the persons to be tested. In other words, variation between the circumstances of each trial or across many tests is virtually non-existent with the exception of the characteristics of the persons taking the tests. In addition, this arrangement may also be less muscle intensive for some persons as lifting a finger at rest may be easier than holding a finger above an input device for test. In other words, the person can be focused on waiting for the stimulus rather than holding his or her finger at a particular location above the touchscreen.

A person, or rather, a test driver, may take a plurality of tests (PVTs) at different times of day during different shifts (e.g. the periods of time during which the test driver is expected to monitor the driving of the vehicle in the autonomous driving mode which may also include one or more breaks in such periods). The reaction times may be sent by the testing system 100 to a remote server computing device such as server computing device 410. This data may be stored, for instance, in the storage system 450.

Figure 6:
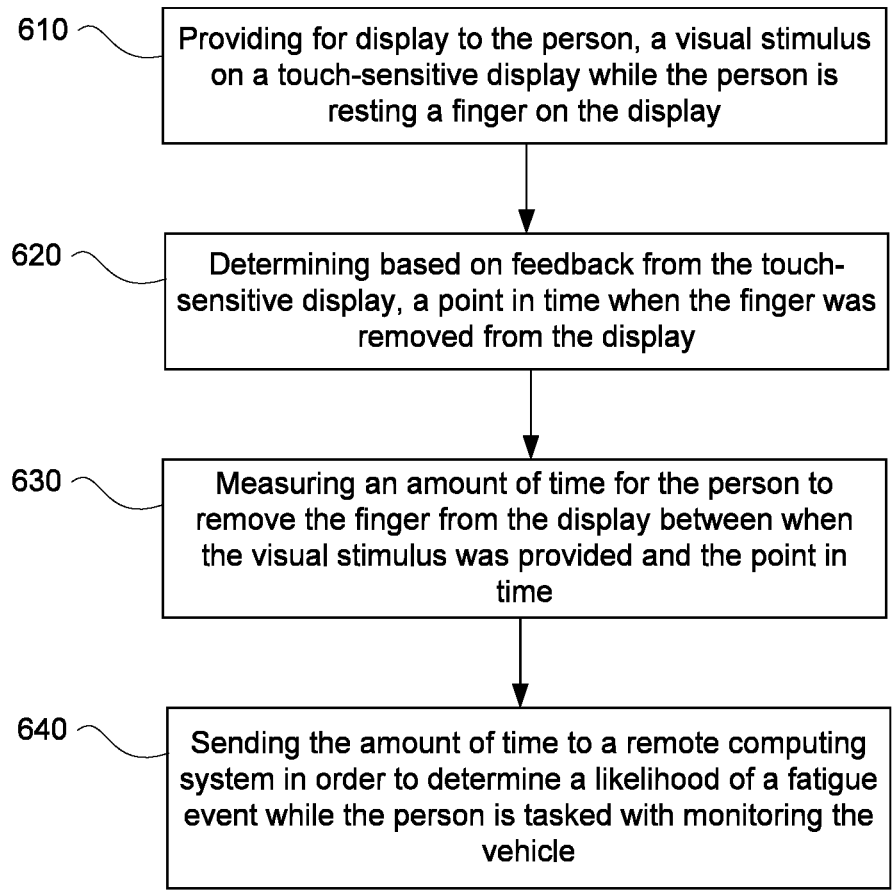
FIG. 6 is an example flow diagram in accordance with aspects of the disclosure.

FIG. 6 is an example flow diagram 600 for administering a psychomotor vigilance test to a person tasked with monitoring a vehicle operating in an autonomous driving mode which may be performed by one or more processors of one or more computing devices, such as the processors 120 of computing devices 110 of the testing system 100. At block 610, a visual stimulus is provided for display on a touch-sensitive display while the person is resting a finger on the display. At block 620, based on feedback from the touch-sensitive display, a point in time when the finger was removed from the display is determined. At block 630, an amount of time for the person to remove the finger from the display between when the visual stimulus was provided and the point in time is measured. At block 640, the amount of time is provided to a remote computing system in order to determine a likelihood of a fatigue event while the person is tasked with monitoring the vehicle. Each stimulus and amount of time correspond to a single trial, and wherein the test includes a plurality of trials. In addition, the test may also include providing instructions to the person to place the finger on the display prior to providing the visual stimulus.

In some instances, a plurality of trials from a single PVT may be scored by the server computing devices 410 and/or the computing device 110 and thereafter sent to the server computing devices 410. The scores may also be stored in the storage system 450.

The scoring may be determined based on the response times. In one example, if a threshold amount of time is 300 milliseconds, and a reaction time less than 355 milliseconds, the test driver may be considered to have passed. If the response time is greater than 355 milliseconds, the test driver may be considered to have failed or to have a lapse in his or her attention. As another example, if the test driver's response time is measured within 100 milliseconds of, or before, a stimulus for a trial is displayed or played, the test driver may also be considered to have failed or to have had a lapse. In this regard, the 100 milliseconds may also identify false response times as 100 ms corresponds the transmission limits of a human nervous system. In situations where false response times or "false starts" are prevalent, the test may be disregarded and administered again or the trial may simply be identified as a failure. A ratio of the number of passed or failed trials to the total amount of trials in a test which represents the passenger's rate of passing or failing for the test may be determined. Thus, the ratio may provide a score on a scale of 0 to 1. Other scoring methods may also be used.

This information may be combined with other signals. For instance, the remote monitoring system 280 may be used to determine a test driver's fatigue. For example, as noted above, the remote monitoring system 280 may include one or more video or still cameras which provide a remote assistance operator, such as people 422, 432, 442, to "check in" on the test driver while he or she is monitoring a vehicle, such as vehicle 200. For instance, the remote assistance operator may identify signals such as a test driver "nodding off", slowly closing his or her eyes, not monitoring the road with his or her eyes, etc. This same video or camera data may also be used by an automated system (e.g. an in-vehicle monitoring system) to look for similar signals. As another instance, the testing system may include an option for a test driver to self-report the state of his or her fatigue on the same or a different assessment scale, such as entering a value on a scale of 0 to 1, 0 to 10, 0 to 100, etc. This fatigue information may also be stored in the storage system 450. As yet another example of other signals, patterns in the time-to-reset (TTR) may also cause fatigue. In other words, the time it takes for the driver to put his or her finger back on the display, before each task can increase over time. Thus, fatigue could product longer TTRs due to lapses in vigilance.

Results from a particular test driver's PVTs as well as the other signals may be used to train a model to determine parameter values for that particular test driver. Alternatively, rather than being for a particular test driver, the model may be trained for a similarly situated test driver. For example, drivers whose baseline PVT performance (i.e. scores) is very similar to other drivers may be grouped together, and the results from the PVTs of these drivers as well as the other signals may be used to train a model. In this regard, the model may produce a set of parameters effective at detecting fatigue for that group specifically. The model may be a regression model, neural network, random forest or any other predictive model that can produce a numerical prediction on a scale. The model may be trained by one or more server computing devices, such as the server computing devices 410.

Figure 7:
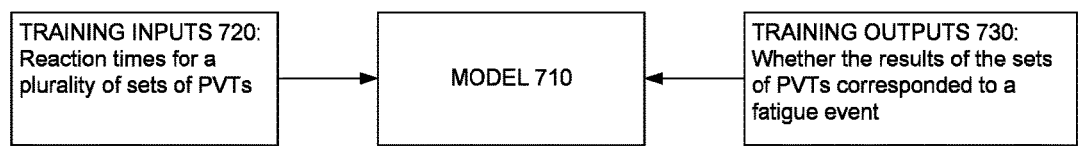
FIG. 7 is an example block diagram representing training of a model in accordance with aspects of the disclosure.

FIG. 7 is an example representation of training a model 710 for a particular test driver, though similar approaches may be used for training a model for similarly situated test drivers. PVT data for the particular test driver may be used as training inputs 720. The PVT data may include both the dates, times, and point in time relative to the particular test driver's shift that a series of PVTs was performed as well as the response times and/or scores.

The data from the remote monitoring system and/or the self-reported data for that particular test driver may be used to determine whether a set of PVTs corresponds to a fatigue event (e.g. stop paying attention or even fall asleep). For instance, PVT data may be correlated (for example, manually) with the other signals in two groups: those that corresponded to a later fatigue event during the same shift and those that did not. These determinations (fatigue event or no fatigue event) may be used as the training outputs 730. The training may produce parameter values for the model that are useful for predicting fatigue events for the particular test driver.

Alternatively, the model may be a statistical model that relates PVT data with a likelihood of a fatigue event for a particular test driver. This may be most useful when there is not a lot of training data for a particular test driver.

The model may be trained such that inputting new PVT data and point in time with respect to his or her shift will provide an estimate of a test driver's current and/or future state of fatigue. For instance, by looking at reaction times immediately before or right after the start of a shift, the model may be able to do a better job of predicting a test driver's future fatigue (e.g. later in the shift). In some instances, the training data may also include additional information such as where a test driver is with respect to his or her circadian rhythm, time since the test driver's last break (or "time on task" corresponding to the duration of time that the test driver has spent monitoring the vehicle uninterrupted) such that this information may also be used as input to the model to provide an estimate of a test driver's current and/or future state of fatigue. This estimate may be a value, for instance on a scale of 0 to 1 which represents a probability that the test driver will have a fatigue event (e.g. stop paying attention or even fall asleep). The more PVT data and other signals used to train the model the more accurate the estimations of the probability that the test driver will have a fatigue event. The model may then be associated with the test driver, for instance using an identifying code or other information, and saved for later retrieval in the storage system 450.

Figure 8:
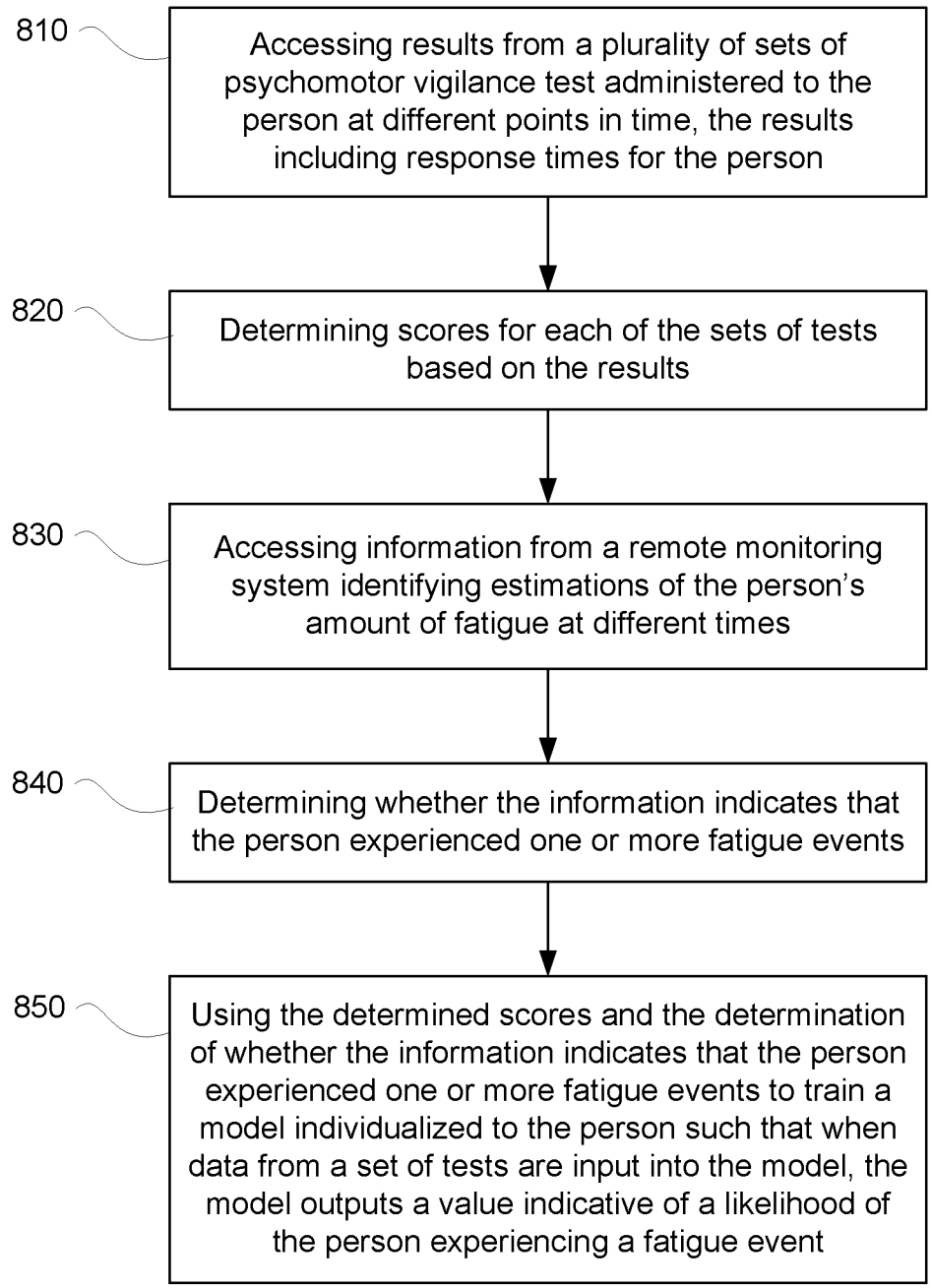
FIG. 8 is an example flow diagram in accordance with aspects of the disclosure.

FIG. 8 is an example flow diagram 800 for training a model for estimating a likelihood of a fatigue event for a person tasked with monitoring a vehicle operating in an autonomous driving mode which may be performed by one or more server computing devices, such as the server computing devices 410. At block 810, results from a plurality of sets of psychomotor vigilance test administered to the person at different points in time are accessed. The results include response times for the person. At block 820, scores for each of the sets of tests are determined based on the results. At block 830, information from a remote monitoring system (or an in-vehicle monitoring system) identifying estimations of the person's amount of fatigue at different times is accessed. At block 840, whether the information indicates that the person experienced one or more fatigue events is determined. At block 850, the determined scores and the determination of whether the information indicates that the person experienced one or more fatigue events are used to train a model individualized to the person such that when data from a set of tests are input into the model, and the model outputs a value indicative of a likelihood of the person experiencing a fatigue event. As noted above, the training may provide parameter values for the model for the person. When using the parameter values, the model may output a value indicative of a likelihood of the person experiencing a fatigue event.

When and how often the testing system administers a test may vary depending upon the situation. For instance, a test may be initiated when a vehicle is stopped, such as at the beginning or the end of a test driver's shift, immediately before or after the test driver goes on a break, etc. In addition, the testing may be performed more often during night time shifts than day time shifts. To administer a test, the vehicle's computing devices may send a signal to the testing system when such situations occur. The rate at which tests are administered may be higher at the start of a shift or towards the end of a shift. In this regard, the server computing devices may have access to information about the vehicle that each test driver is tasked with monitoring as well as information about the start and end of each test driver's shifts. In other instances, the aforementioned other signals, such as a remote assistance operator or automated monitoring system may determine that the test driver is experiencing or is likely to experience a fatigue event. The remote assistance operator or remote monitoring system may cause a signal to be sent to the testing system to administer a test.

The testing system may test a test driver by administering a set of trials and evaluating the test driver's response times for those trials as described above. The response times as well as date and time information for the trials of a test, shift information about the relative point in the test driver's shifts, as well as any of the additional information discussed above (if available) may then be sent to and received by the remote server computing device.

The remote server computing device may then use the reaction times to determine whether the test driver passed or failed each of the set of trials of a test. In this context, failing (as discussed above) may indicate that the test driver is not sufficiently alert to competently monitor the autonomous vehicle. The server computing device may also determine a score for the trials of the set. To do so, the remote server computing device may compare the reactions times to a threshold amount of time and determine a ratio as described above.

The model associated with the particular test driver, which as noted above, was trained using data from prior tests administered to that test driver as well as other signals as discussed above may be identified. The results of the determinations of whether the test driver passed or failed each PVT of the set of PVTs or alternatively, the response times, may be input into the model in order to determine a value representative of a likelihood of a fatigue event. In other words, the ratio as well as the date and time information, shift information, and any of the additional information may be input into the model for that particular test driver to assess whether that particular test driver is likely to have a fatigue event by providing a value as indicated above. Analyzing the data at the server computing devices 410 may provide flexibility to quickly change logic, thresholds, etc., and also to allow remote assistance operators, the server computing devices, or others to require a given test driver to take another test as soon as possible (e.g. at a next break). In addition, the model can be sensitive to recent data, aggregated at the server computing devices 410 (or storage system 450). For example, if the most recent data from the remote monitoring system 280 also suggests fatigue, the same level of test performance (e.g. score) may result in a higher probability of there being a fatigue event.

In order to determine and initiate an intervention response, the value may then be compared by the server computing devices 410 to a threshold value or plurality of threshold values to determine whether and what type of intervention response to take. The threshold values or plurality of threshold values may be hand-tuned or selected depending upon precision and recall values desired for the PVT system. In other words, the thresholds may be lower (e.g. lower values) in order to increase the amount or magnitude of intervention responses or higher (e.g. higher values) in order to decrease the amount or magnitude of intervention responses. Once an intervention response is identified, the server computing devices may send a signal to the computing devices of the vehicle, the PVT system, and/or a remote assistance operator in order to initiate the identified intervention response.

Various different types of intervention responses may be employed. For instance, intervention responses may include providing with supportive options and, if applicable, task-reassignment. For example, the test driver may be provided with another test or another set of trials, may be connected with one of the remote assistance operators who can interact with the test driver as discussed above, or may even be relieved of the duty of monitoring a vehicle for a current shift. In this regard, the tests and the model can be used by the server computing devices 410 to automatically determine whether a test driver should be task-reassigned before or even during a shift. In some instances, depending on the test driver's overall test performance, the test driver may be automatically or discretionarily assigned to less safety-critical task or the vehicle may even prevent the test driver from controlling the vehicle in the manual driving mode based on the signal. For example, the test driver may also be assigned to tasks associated with improved alertness, such as rest periods or tasks with higher engagement. In cases where a test driver has some indicators of fatigue but is still below a lower value threshold as described above, additional in-car or remote monitoring may be added to improve fatigue detection should a fatigue event occur.

The scoring for a particular test driver (which may be used as input to the model) may also be adjusted based on past performance and/or physical fatigue. For example, some test drivers may have faster reflexes even when they are tired, and other test drivers may experience increases in response time due to physical fatigue. In this regard, these test drivers may have the same reaction time, but different response times. As such, the threshold amount of time used to determine whether a test driver passed or failed a particular trial may be adjusted. In order to do so, a model of how this test driver or similarly situated test drivers (same time of day, same part of a shift, etc.) reaction times change over time may be generated. The model may be a statistical regression model which provides another way to separate performance variance due to fatigue from variance that is due to other factors. In another example, although each trial of a PVT is very short in duration (e.g. merely lifting a finger), it does require physical movement which over time will vary in response time due to accumulating fatigue (i.e. the muscles of the test driver's finger will become fatigued, even if the test driver has not). Thus, over time, the threshold amount of time used to determine whether a test driver has passed or failed a trial may be increased according to the fluctuations in the model.

In addition, depending upon the orientation of the touchscreen, the test may be more or less prone to physical fatigue. For instance, if the touchscreen is oriented in an upright position, the test driver may be more prone to muscle fatigue because he or she must hold his or her arm in an elevated position. As another example, a driver with a longer reach may incur physical fatigue faster than one with a shorter reach, who may compensate by leaning toward the touch-sensitive display or other user input device used to administer the trials. This, data may also be included in the model for determining the threshold amount of time.

Similarly, depending on the hand-dominance of the test driver, variance may differ as the physical posture differs for left-handed persons and right-handed persons. In this regard, there may be different models for determining the threshold amount of time for left-handed persons versus right-handed persons. Again, the left-handed person or right-handed person models may be specific to this test driver, similarly situated test drivers (same time of day, same part of a shift, etc.), or all test drivers.

Figure 9:
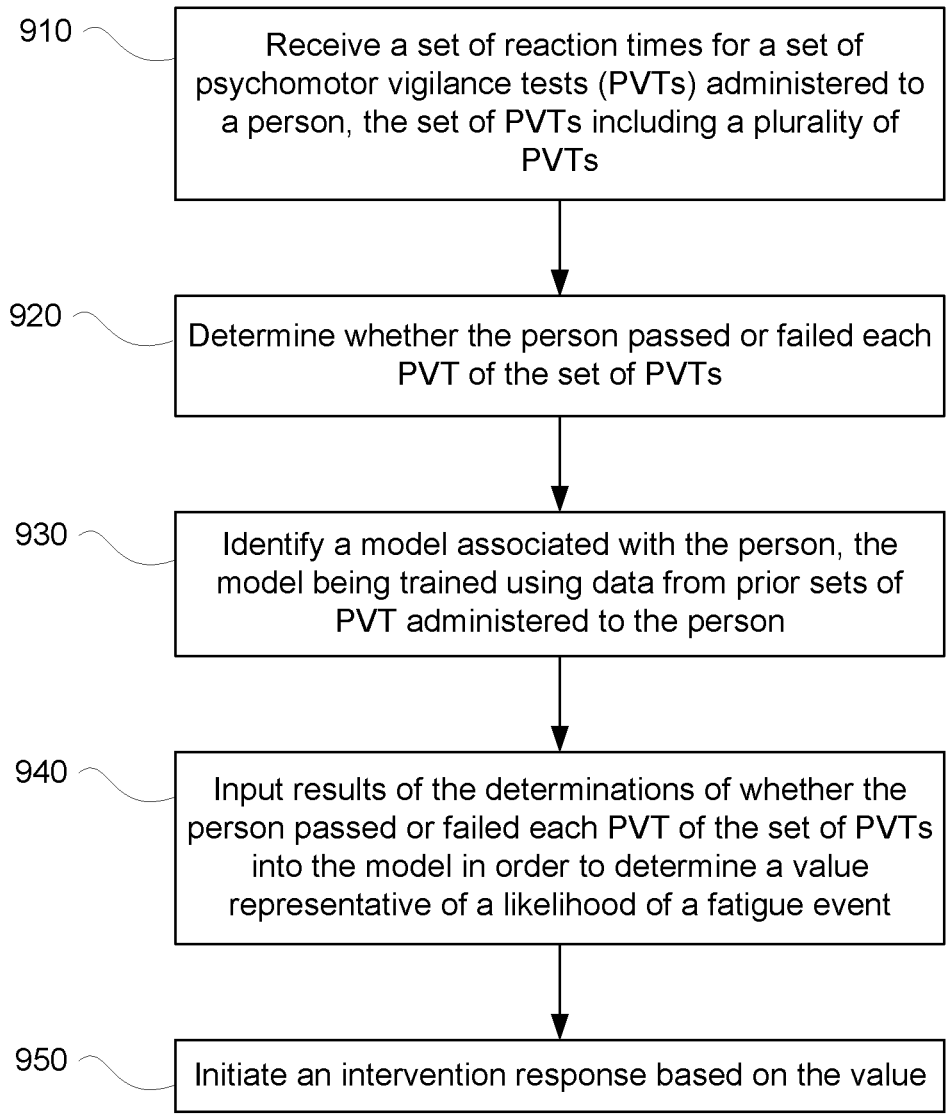
FIG. 9 is an example flow diagram in accordance with aspects of the disclosure.

FIG. 9 is an example flow diagram 900 for assessing a likelihood of a person experiencing a fatigue event when the person tasked with monitoring a vehicle operating in an autonomous driving mode which may be performed by one or more server computing devices, such as the one or more server computing devices 410. For instance, at block 910, a set of response times for a psychomotor vigilance test administered to the person is received. The test includes a plurality of trials. At block 920, whether the person passed or failed each trial of the set of trials is determined. At block 930, a model associated with the person is identified. The model was trained using data from prior psychomotor vigilance tests administered to the person. At block 940, results of the determinations of whether the person passed or failed each trial of the set of trials are input into the model in order to determine a value representative of a likelihood of a fatigue event. At block 950, an intervention response is initiated based on the value.

The features described herein may provide for a reliable and effective system for identifying possible fatigue events in persons tasked with monitoring the driving of a vehicle operating in an autonomous driving mode. For instance, because the model is trained specific to a particular person or a similarly situated person, the model may be more likely to identify outlier situations. For example, if a particular person has an average score of 0.8 at a particular time of day over the last three months, but then at one time, that same person scores a 0.7 which may be one or more standard deviations outside of the normal performance for that person, the model may still indicate that the person is likely to have a fatigue event even though a score of 0.7 may have been considered acceptable under a more generalized standard. Moreover, because the threshold amount of time used to determine whether a person has passed or failed a particular PVT can be adjusted to accommodate for the particular person or similarly situated persons, this may further increase the effectiveness of the system reduce false positives. In other words, threshold amounts of time may be set in a way that accounts for individual variance, for instance, due to muscle fatigue.

Unless otherwise stated, the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements.

The invention claimed is:

1. A method of assessing a likelihood of a person experiencing a fatigue event, the person tasked with monitoring a vehicle operating in an autonomous driving mode, the method comprising: receiving, by one or more server computing devices, a set of response times for a set of trials of a psychomotor vigilance test (PVT) administered to the person; determining, by the one or more server computing devices, whether the person passed or failed each trial of the set of trials; identifying, by the one or more server computing devices, a PVT model associated with the person from a plurality of PVT models associated with a plurality of respective persons, wherein each respective PVT model of the plurality of PVT models is trained using data from prior PVTs administered to the respective person; inputting, by the one or more server computing devices, results of the determinations of whether the person passed or failed each trial of the set of trials into the identified PVT model in order to determine a value representative of a likelihood of a fatigue event; and initiating, by the one or more server computing devices, an intervention response based on the value.

2. The method of claim 1, further comprising determining the intervention response by comparing the value to one or more threshold values.

3. The method of claim 1, further comprising determining a score for the PVT based on the determinations of whether the person passed or failed each trial of the set of trials, wherein the results include the score.

4. The method of claim 3, wherein the score represents a passing or failing rate for the person.

5. The method of claim 1, further comprising inputting date and time information for the set of trials into the identified PVT model in order to determine the value.

6. The method of claim 1, further comprising inputting shift information about a relative point in time for a shift for monitoring the vehicle of the person for the PVT into the identified PVT model in order to determine the value.

7. The method of claim 1, further comprising inputting an amount of time since a last break of the person for the PVT into the identified PVT model in order to determine the value.

8. The method of claim 1, further comprising inputting information identifying where the person is with respect to his or her circadian rhythm, for the PVT into the identified PVT model in order to determine the value.

9. The method of claim 1, further comprising determining a threshold amount of time based on whether the person is left-handed or right-handed, and wherein determining whether the person passed or failed each trial of the set of trials is based on the threshold amount of time.

10. The method of claim 1, further comprising determining a threshold amount of time using a model of how response times change over time due to muscle fatigue, and wherein determining whether the person passed or failed each trial of the set of trials is based on the threshold amount of time.

11. The method of claim 1, further comprising determining a threshold amount of time using a model of how response times change over time for the person, and wherein determining whether the person passed or failed each trial of the set of trials is based on the threshold amount of time.

12. The method of claim 1, further comprising determining a threshold amount of time using a model of how response times change over time for a similarly situated person, and wherein determining whether the person passed or failed each trial of the set of trials is based on the threshold amount of time.

13. The method of claim 1, further comprising determining a threshold amount of time is based on an orientation of a user input device used to administer the set of trials, and wherein determining whether the person passed or failed each trial of the set of trials is based on the threshold amount of time.

14. The method of claim 1, wherein initiating the intervention response comprises sending one or more signals to one or more computing devices of the vehicle, a PVT system that administered the PVT, and a computing device of a remote assistance operator.

15. The method of claim 14, wherein the one or more signals include instructions for the PVT system to administer a second PVT.

16. The method of claim 15, wherein the one or more signals include instructions for the vehicle to stop operating in the autonomous driving mode.

17. The method of claim 16, wherein the one or more signals include instructions for the vehicle to prevent the person from operating the vehicle in a manual driving mode.

18. The method of claim 15, wherein the one or more signals enable the person to communicate with the remote assistance operator.

19. The method of claim 1, wherein the one or more server computing devices are further configured to determine a threshold amount of time using a model of how response times change over time for the person, and wherein the one or more server computing devices are further configured to determine whether the person passed or failed each trial of the set of trials further based on the threshold amount of time.

20. A system for assessing a likelihood of a person experiencing a fatigue event, the person tasked with monitoring a vehicle operating in an autonomous driving mode, the system comprising one or more server computing devices configured to:
receive, a set of response times for a set of trials of a psychomotor vigilance test (PVT) administered to the person;
determine, whether the person passed or failed each trial of the set of trials;
identify a PVT model associated with the person from a plurality of PVT models associated with a plurality of respective persons, wherein each respective PVT model of the plurality is trained using data from prior PVTs administered to the respective person;
input results of the determination of whether the person passed or failed each trial of the set of trials into the identified PVT model in order to determine a value representative of a likelihood of a fatigue event; and
initiate an intervention response based on the value.

21. The system of claim 20, further comprising the vehicle.

22. The system of claim 20, wherein the one or more server computing devices are further configured to determine a threshold amount of time based on whether the person is left-handed or right-handed, and wherein the one or more server computing devices are configured to determine whether the person passed or failed each trial of the set of trials further based on the threshold amount of time.

* * * * *